United States Patent
Morgan et al.

(10) Patent No.: US 6,245,066 B1
(45) Date of Patent: *Jun. 12, 2001

(54) ABLATION CATHETER

(75) Inventors: John Mark Morgan, Near Stockbridge; Andrew David Cunningham, Strathclyda, both of (GB)

(73) Assignee: C. R. Bard, Inc., Murray Hill, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/180,636
(22) PCT Filed: May 9, 1997
(86) PCT No.: PCT/GB97/01270
  § 371 Date: Nov. 11, 1998
  § 102(e) Date: Nov. 11, 1998
(87) PCT Pub. No.: WO97/42893
  PCT Pub. Date: Nov. 20, 1997

(30) Foreign Application Priority Data

May 11, 1996 (GB) .................................................. 9609866

(51) Int. Cl.[7] ............................................... B61B 18/18
(52) U.S. Cl. ............................ 606/41; 606/48; 607/101; 607/122
(58) Field of Search ............................... 606/41, 46, 48, 606/50, 32; 600/372, 377; 607/101, 119, 122

(56) References Cited

U.S. PATENT DOCUMENTS

| 452,220 | 5/1891 | Gunning. | |
|---|---|---|---|
| 5,366,476 | * 11/1994 | Noda | 606/206 |
| 5,482,037 | 1/1996 | Borghi | 128/646 |
| 5,578,067 | * 11/1996 | Ekwall et al. | 607/122 |
| 5,720,718 | * 2/1998 | Rosen et al. | 604/22 |
| 5,722,401 | * 3/1998 | Pietroski et al. | 600/374 |
| 5,800,482 | * 9/1998 | Pomeranz et al. | 607/101 |
| 5,885,278 | * 3/1999 | Fleischman | 606/41 |

FOREIGN PATENT DOCUMENTS

| WO94/24931 | 11/1994 | (WO) | A61B/5/04 |
| WO95/18575 | 7/1995 | (WO) | A61B/17/39 |

* cited by examiner

*Primary Examiner*—Linda C. M. Dvorak
*Assistant Examiner*—David M. Ruddy
(74) *Attorney, Agent, or Firm*—Darby & Darby

(57) ABSTRACT

With reference to the figure, an ablation catheter (1) for use in heart surgery comprises a probe (2), a tubular electrode (3) mounted on the probe, so as to axially be slidable relative thereto, and remote-operated actuator means (4) for so sliding the electrode (3). The probe (2) is of electrically-insulating material, and comprises a tip (6), an axially-extending shaft (7), and a rear end portion (8). A surface groove (9) is formed in the probe which extends longitudinally up to the tip (6). The groove (9) locates a conductor (10) which interconnects the electrode (3) with a controllable source (15) of electrical energy and is enclosed in an insulating sheath (16) of flexible construction. The flexible sheath (16), and conductor (10) therein are axially slidable within the groove (9) of the catheter (1). The sheath (16) provides for electrical insulation of the conductor (10) as the electrode (3) is moved along the probe shaft (7). In use, the catheter (1) is employed to create long endocardial lesions in cardiac chambers by application of radio frequency current provided by the source (15). Contiguous lesions are created, in a series of steps, by careful, remote-operated movement of the electrode (3), and energization of the same.

16 Claims, 2 Drawing Sheets

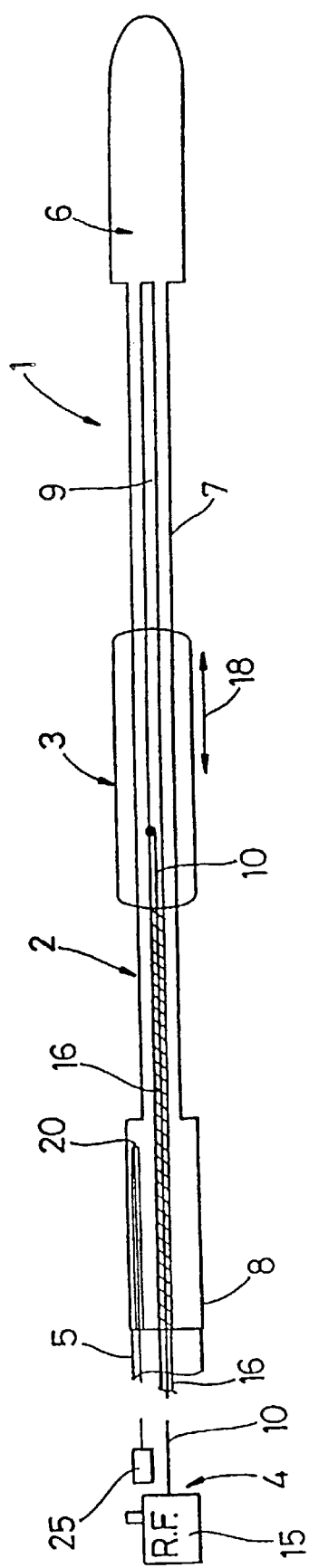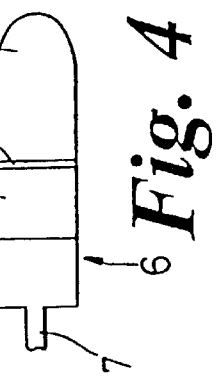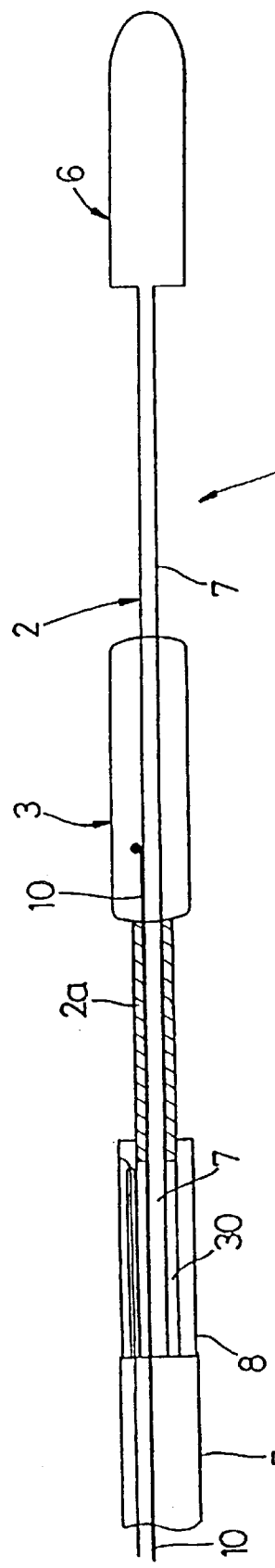
Fig. 1
Fig. 4
Fig. 3

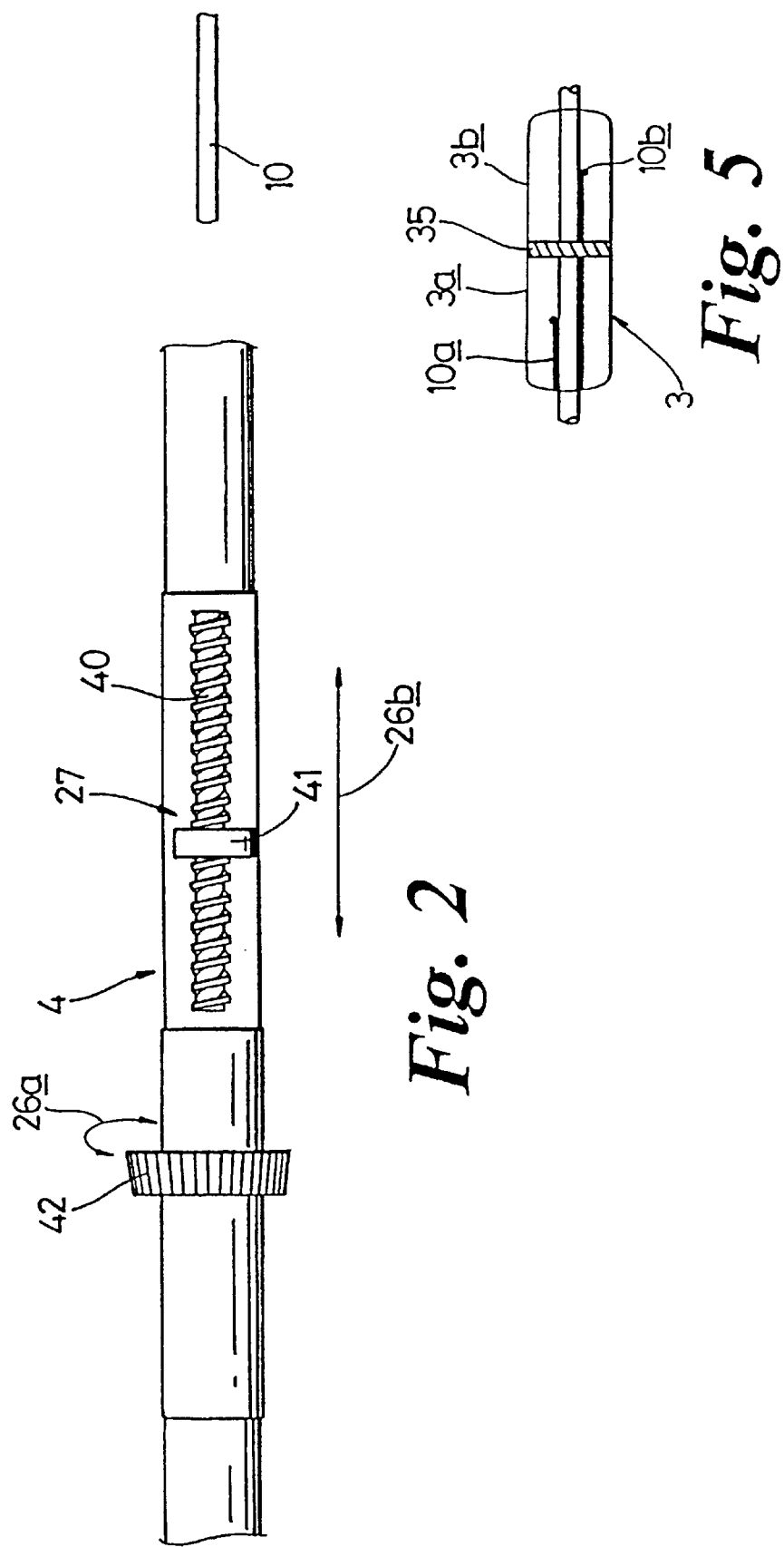

ABLATION CATHETER

This is a continuation of application Ser. No. 09/180,636, filed Nov. 11, 1998 which is the U.S. National Phase of PCT Application No. PCT/GB97/01270, filed May 9, 1997. The most recent of these prior applications is hereby incorporated herein by reference, in its entirety.

This invention relates to ablation catheters and particularly, but not exclusively, to an ablation catheter suitable for use in medical procedures related to the treatment of heart disease.

For example, the catheter may be used to cause limited and localised damage in cardiac chambers, by employment of radio frequency energy.

WO-A-951875 (FIG. 9) discloses an ablation catheter comprising a hollow sleeve-like probe, an elongate electrode slidably located by the bore of the probe so as to be movable relative thereto, and remote-operated actuator means for moving the electrode axially within the bore of the probe.

According to the present invention, an ablation catheter comprises a probe, an electrode carried by a shaft portion of the probe so as to be movable relative thereto, and remote-operated actuator means for moving the electrode, characterised in that the electrode is slidably mounted on the exterior of the shaft portion, so as to be movable axially relative thereto.

An elongate conductor is preferably connected to the electrode, and insulation means is preferably provided around the conductor.

The insulation means may comprise a tubular sheath which extends substantially from the remote-operated actuator means to the electrode, and is housed in a longitudinal channel in the probe. Axial sliding movement of the electrode is preferably then arranged to be effected by axial movement of the sheathed conductor at the end thereof remote from the electrode.

Various embodiments of the invention will now be described, by way of example only, with reference to the accompanying drawings, wherein:

FIG. 1 is a fragmentary side view, partly in section, of an ablation catheter in accordance with the invention, FIG. 2 is a fragmentary view, on an enlarged scale, which illustrates a modification, FIG. 3 is a fragmentary side view of an alternative embodiment employing a mobile insulation sleeve, and FIG. 4 is a side elevation of a modified probe tip incorporating additional bipolar sensing electrodes; and FIG. 5 is a side elevation of a two-part electrode.

With reference to FIG. 1, an ablation catheter 1 for use in heart surgery comprises a probe 2, a tubular electrode 3 mounted on the probe, so as to axially be slidable relative thereto, and remote-operated actuator means 4 for so sliding the electrode 3.

The catheter 1 also comprises a flexible tube or shaft 5 forming an extension of the probe 2.

The flexible tube/shaft 5 and the probe 2 are of electrically-insulating material, and comprise a tip 6, an axially-extending shaft 7 and a rear end portion 8 to which the flexible tube 5 is attached.

A surface groove or channel 9 is formed in the end portion 8 and shaft 7, and extends longitudinally up to the tip 6, or near to the tip 6.

The channel 9 locates a conductor 10 which interconnects the electrode 3 with a controllable source 15 of (in this example) radio frequency energy. The conductor 10 is enclosed in an insulating sheath 16 of flexible construction.

The flexible sheath 16, and conductor 10 therein are axially slidable within the channel 9 of the catheter 1. This provides for electrical insulation of the conductor 10 as the electrode 3 is moved along the probe shaft 7. The conductor 10 and sheath 16 are long enough to allow for this movement of the electrode 3.

The illustrated electrode 3 is of tubular and cylindrical form (but in alternative embodiments could be of ovoid, spherical or other geometry) so that it is slidable along the probe shaft 7, as indicated by the double-headed arrow 18. The material of the electrode 3 is of electrically-conducting metal or alloy.

With reference to FIG. 5, the movable electrode 3 may, if desired, may be of multi-component form and comprise independent components 3a, 3b connected to independent conductors 10a, 10b respectively, and insulated from each other by insulation 35. The conductors 10a, 10b are connected to the controllable R.F. source 15.

The actuator mechanism 4 which provides for movement of the electrode 3 is connected to the conductor 10 (or 10a, 10b) by means of a sliding mechanism, ratchet mechanism (for example worm screw attachment to the terminal portion of conductor 10) or other mechanism so that operation of this actuator causes axial displacement of the conductor 10 and thereby axial displacement of electrode 3, which is moved along the probe shaft 7 towards the end portion 8 from an initial position closer to the tip 6, or vice versa.

The portion of the probe over which the electrode 3 is displaced may be coated with a hydrophobic or similar substance in order to lubricate the displacement of the catheter.

FIG. 2 shows an example of a suitable ratchet mechanism 27, which comprises a worm screw 40, the teeth of which are engaged by a worm wheel 41, whereby manual rotation of the wheel causes axial movement of the worm screw 40 and thereby corresponding axial movement of the conductor 10 and electrode 3.

Using established technology in the construction of deflectable ablation catheters, the portion of the probe shaft 7 over which the electrode 3 slides, may be flexed, extended, or rotated by axial or rotational displacement of a collar 42 fixed to the actuator mechanism 4, as indicated by the double headed arrows 26a, 26b.

In an alternative arrangement, a replaceable stylet 20 may be fitted in the end portion 8 of the probe 7. This allows a range of stylets having different end curvatures to be introduced into the end portion 8 and advanced to the probe tip, so as to produce curvatures of that portion of the probe shaft 7 over which the electrode slides.

It will be appreciated that actuating means 4 or 27, like the source 15, are located remote from the catheter tip 6.

In the application of the invention, the catheter 1 is employed to create long endocardial lesions in cardiac chambers or long epicardial lesions on the outer surface of the cardiac chambers by application of radio frequency current provided by the source 15. Contiguous lesions are created, in a series of steps, by careful, remote-operated movement of the electrode 3, and delivery of energy thereto (from source 15) at each position.

Temperature control during lesion production may be effected by using standard components such as thermocouples or thermisters, embedded in the electrode 3 or in a catheter shaft disposed nearby.

In an alternative embodiment, direct current or other energy may be employed as an alternative to alternating radio frequency current.

Other suitable forms of heat energy comprise laser energy and microwave energy.

In FIG. 3 parts corresponding to those of the embodiment of FIG. 1 have been given like reference numerals.

In the alternative embodiment of FIG. 3, instead of groove 9, the conductor 10 extends through an axially retractable insulation collar 2a which slides over the shaft of the catheter. As shown in FIG. 3, the collar 2a abuts with electrode 3 and is retractable in part within an annular blind bore 30 in the end portion 8 on leftward movement in FIG. 3 of the electrode from the initial position, shown. This is intended to facilitate easier assembly of the ablation catheter.

In the modification of FIG. 4, the tip 6 incorporates an annular electrode 28 and a tip electrode 29, the electrodes 28, 29 being electrically insulated from each other by insulation 30. However, a single electrode may be provided if desirable, or even no electrode.

Components of the catheter probe which are to be inserted into the body may be coated, except for the electrode 3, with chemicals which have anticoagulation properties. For example, Heparin or Ticlopidine, or related compounds.

Electrical connections may be provided between one or more of the electrodes 3, 28, 29 and sensitive amplifiers, whereby electrical signals emitted by the heart may be displayed on an electronic screen, and condition of the heart monitored thereby.

What is claimed is:

1. An ablation catheter comprising:
   (1) a probe having a shaft which defines an exterior surface and a channel in at least a portion thereof;
   (2) an electrode carried on the exterior surface of the probe so as to be axially movable relative thereto;
   (3) a conductor mounted for axially slidable movement within the channel and connected to the electrode and extending proximally to a source of energy; and
   (4) remote-operated actuator means connected to the conductor for axially moving the electrode along the exterior of the shaft portion in response to the actuator means.

2. An ablation catheter as claimed in claim 1, wherein said electrode is of tubular form and embraces the shaft portion of the probe.

3. An ablation catheter as claimed in claim 1, wherein said electrode is of ovoid form.

4. An ablation catheter as claimed in claim 1, wherein said movable electrode is of multi-electrode component form.

5. A catheter as claimed in claim 1, wherein the conductor connected to the electrode is elongate.

6. An ablation catheter as claimed in claim 5, wherein insulation is provided around said elongate conductor.

7. An ablation catheter as claimed in claim 6, wherein said insulation comprises a tubular sheath which extends substantially longitudinally from the remote-operated actuator means to the electrode and is housed in a longitudinal channel formed in the probe.

8. An ablation catheter as claimed in claim 7, wherein axial sliding movement of said electrode is effected by axial movement of the sheathed conductor at the end thereof remote from the electrode.

9. An ablation catheter as claimed in claim 7, wherein the longitudinal channel comprises a surface groove formed in the exterior of the probe.

10. An ablation catheter as claimed in claim 1, wherein the probe has a tip, at least part of which incorporates an electrode.

11. An ablation catheter as claimed in claim 10, wherein the electrode incorporated in the probe tip is disposed at the forward end thereof.

12. An ablation catheter as claimed in claim 5, wherein the remote-operated actuator means is operable to cause axial displacement of said elongate conductor and thereby axial displacement of the electrode connected thereto.

13. An ablation catheter as claimed in claim 1, wherein said remote-operated electrode actuator means comprise a ratchet mechanism.

14. An ablation catheter as claimed in claim 1, wherein the non-electrode parts thereof are coated with anti-coagulation material.

15. The combination of an ablation catheter as claimed in claim 1, and a controlled source of energy connected thereto.

16. The combination of claim 13, wherein the source of energy comprises a source of radio frequency electrical energy, laser energy or microwave energy.

* * * * *